(12) United States Patent
Myhren et al.

(10) Patent No.: US 6,384,019 B1
(45) Date of Patent: May 7, 2002

(54) GEMCITABINE DERIVATIVES

(75) Inventors: Finn Myhren, Porsgrunn; Bernt Børretzen, Heistad; Are Dalen, Trondheim; Marit Liland Sandvold, Porsgrunn, all of (NO)

(73) Assignee: Norsk Hydro ASA, Oslo (NO)

( * ) Notice: Subject to any disclaimer, the term of this patent is extended or adjusted under 35 U.S.C. 154(b) by 0 days.

(21) Appl. No.: 09/355,112

(22) PCT Filed: Jan. 23, 1998

(86) PCT No.: PCT/NO98/00020

§ 371 Date: Sep. 15, 1999

§ 102(e) Date: Sep. 15, 1999

(87) PCT Pub. No.: WO98/32762

PCT Pub. Date: Jul. 30, 1998

(30) Foreign Application Priority Data

Jan. 24, 1997 (GB) .............................................. 9701427

(51) Int. Cl.⁷ .............................................. A61K 31/70
(52) U.S. Cl. .......................... 514/49; 514/50; 536/28.2; 536/28.5; 536/28.51
(58) Field of Search ..................... 514/49, 50; 536/28.2, 536/28.5, 28.51

(56) References Cited

U.S. PATENT DOCUMENTS 5,061,793 A * 10/1991 Grindley et al.
5,401,838 A * 3/1995 Chou
5,464,826 A * 11/1995 Grindley et al.

FOREIGN PATENT DOCUMENTS

EP 0693077 * 1/1996

OTHER PUBLICATIONS

Hertel et al., J. Org. Chem., vol. 53, No. 11, pp. 2406–2409 (1988).*

* cited by examiner

*Primary Examiner*—James O. Wilson
(74) *Attorney, Agent, or Firm*—Fitzpatrick, Cella, Harper & Scinto

(57) ABSTRACT

The invention provides Gemcitabine esters or amides in which the 3'- and/or 5'-OH group and/or the $N^4$-amino group is derivatised with a $C_{18}$- and/or $C_{20}$-saturated or mono-unsaturated acyl group, preferably an acyl group selected from oleoyl, elaidoyl, cis-eicosenoyl and trans-eicosenoyl. The Gemcitabine esters and amides are useful as anti-cancer and anti-viral agents.

32 Claims, No Drawings

GEMCITABINE DERIVATIVES

This invention relates to certain long chain saturated and monounsaturated fatty acid derivatives of 2',2'-difluorodeoxycytidine (Gemcitabine), and to pharmaceutical compositions containing them. Gemcitabine has the 5 formula:

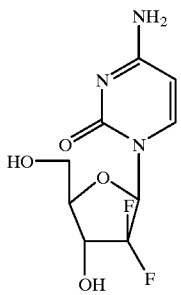

Gemcitabine is a nucleoside analogue which has shown effect for the treatment of neoplastic conditions in both in vitro and in in vivo studies. (New anticancer agents, Weiss et al, Cancer Chemotherapy and Biological Response Modifiers Annual 16, editors Pinedo, Longo and Chabner, 1996. Elsevier Science B. V., Supplement to Seminars in Oncology, Vol. 22, No. 4, Suppl. 11, 1995, editors Yarbro et al. Gemcitabine Hydrochloride: Status of Preclinical Studies). A beneficial effect has also been observed in the clinical development of Gemcitabine. In these studies both the clinical and side effects of Gemcitabine are highly schedule dependent. (Seminars in Oncology, Vol. 22, No. 4, Suppl. 11, 1995, pp 42–46).

Gemcitabine is activated inside the cell by deoxycytidine kinase to its active form, the triphosphate of Gemcitabine (dFdCTP). Parallel to this Gemcitabine is deactivated by deoxycytidine deaminase to the corresponding uracil derivative (inactive).

We have now surprisingly found that certain fatty acid derivatives of Gemcitabine have a totally altered pharmacokinetics and tissue distribution. Especially will this be the case with malignant diseases in the RES, lungs, pancreas, intestines, esophagus, uterus, ovaries, melanoma and mammae.

The compounds of the present invention can be represented by the formula I:

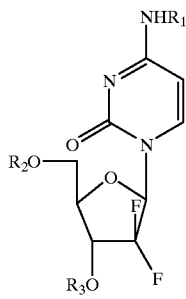

(I)

wherein $R_1$, $R_2$ and $R_3$ are independently selected from hydrogen and $C_{18}$- and $C_{20}$-saturated and monounsaturated acyl groups, with the proviso that $R_1$, $R_2$ and $R_3$ cannot all be hydrogen.

Gemcitabine has three derivatisable functions, namely the 5'- and 3'-hydroxyl groups and the $N^{4-}$ amino group. Each group can selectively be transformed into an ester or amide derivative, but di-adducts (di-esters or ester-amides) and tri-adducts may be formed as well. In the case of the di-and tri-adducts the acyl substituent groups need not necessarily be the same.

Currently, the mono-acyl derivatives of this invention, i.e. with two of $R_1$, $R_2$ and $R_3$ being hydrogen, are preferred. It is especially preferred that the monosubstitution with the acyl group should be in the 3'-O and 5'-O positions of the sugar moiety, with 5'-O substitution being most preferred.

The double bond of the mono-unsaturated acyl groups may be in either the cis or the trans configuration, although the therapeutic effect may differ depending on which configuration is used.

The position of the double bond in the monounsaturated acyl groups also seem to affect the activity. Currently, we prefer to use esters or amides having their unsaturation in the $\omega$-9 position. In the $\omega$-system of nomenclature, the position $\omega$ of the double bond of a monounsaturated fatty. acid is counted from the terminal methyl group, so that, for example, eicosenoic acid ($C_{20}:1_\omega$-9) has 20 carbon atoms in the chain and a single double bond is formed between carbon 9 and 10 counting from the methyl end of the chain. We prefer to use esters, ester-amides and amides derived from oleic acid ($C_{18}:1_\omega$-9, cis), elaidic acid ($C_{18}:1_\omega$-9, trans), eicosenoic acid(s) ($C_{20}:1_\omega$-9, cis) and ($C_{20}:1_\omega$-9, trans), and the amides and 5'-esters are currently the most preferred derivatives of this invention.

Esters, ester-amides and amides of Gemcitabine derived from stearic acid ($C_{18}:0$) and eicosanoic acid ($C_{20}:0$) are advantageously used in some cases.

The derivatives of Gemcitabine according to this invention may generally be prepared according to the following reaction equation:

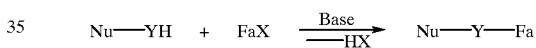

wherein Nu—YH stands for Gemcitabine, Y is oxygen at the 3' and/or 5' position of the sugar moiety or nitrogen at the 4 position of the pyrimidine moiety of Gemcitabine, Fa is an acyl group of a monounsaturated $C_{18}$ or $C_{20}$ fatty acid, and X is a leaving group, for example Cl, Br, 3-thiazolidine-2-thione or OR' wherein R' is Fa, $COCH_3$, COEt or $COCF_3$. Thus, the reaction proceeds by acylation of the nucleoside. This is accomplished by the use of suitable reactive derivatives of fatty acids, especially acid halides or acid anhydrides.

Generally, a proton scavenger needs to be present in order to mop up the acid HX which is liberated by the reaction. Thus, a base may be added to the reaction mixture. For example, when an acid halide such as an acid chloride is used, a tertiary amine base, such as triethylamine, N,N-dimethylaniline, pyridine or N,N-dimethylaminopyridine can be added to the reaction mixture to bind the liberated hydrohalic acid. In other cases, a solvent used in the reaction may serve as the proton scavenger.

Normally, the acylation reaction proceeds without the need for a catalyst. The reactive fatty acid derivative FaX may, in some cases, be formed in situ by means of coupling reagents such as N,N'-dicyclohexylcarbodiimide (DCC), N-ethyl-N'-(3-dimethylaminopropyl)carbodiimide (EDC) or O-(1H-benzotriazol-1-yl)-N,N,N',N'-tetramethyluronium tetrafluoroborate(TBTU).

The reactions are preferably carried out in an unreactive solvent such as N,N-dimethylformamide or a halogenated hydrocarbon, such as dichloromethane. If desired any of the above mentioned tertiary amine bases may be used as solvent, taking care that a suitable excess is present. In this case a separate proton scavenger is not needed. The reaction should preferably be kept between 5° C. and 25° C. After a period of 1 to 60 hours, the reaction will be essentially completed. The progress of the reaction can be followed using thin layer chromatography (TLC) and appropriate solvent systems. When the reaction is completed as determined by TLC, the product can be extracted with an organic solvent and purified by chromatography and/or recrystallization from an appropriate solvent system. As more than one hydroxyl group and also an amino group are present in Gemcitabine, a mixture of acylated compounds may be produced. If required, the individual mono- and multi-acylated derivatives required may be separated by, for instance, chromatography, crystallization, supercritical extraction, etc.

When it is desired to prepare a multi-acyl compound of formula I, in which $R_1$ and/or $R_2$ and/or $R_3$ are the same acyl group, it is preferred to employ the above method(s) using the appropriate acyl-reagent(s) in excess.

In order to prepare multi-acyl compounds of formula I, in which $R_1$ and/or $R_2$ and/or $R_3$ are different, it is preferred to employ the above methods in a stepwise manner with the appropriate choice of reagent. It is also possible to employ properly chosen protecting groups to ensure a specific reaction. A selection of these methods is shown in Scheme 1 below. Any combination of the methods may be employed to prepare a specific product.

Scheme 1

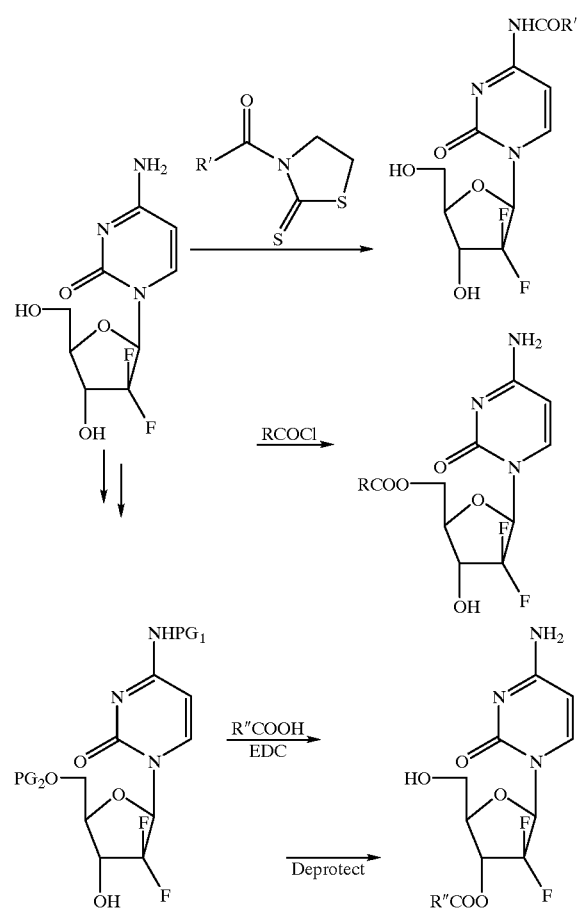

The following Examples illustrate the preparation of two preferred Gemcitabine derivatives of this invention.

EXAMPLE 1

Elaidic Acid (5')-Gemcitabine Ester

To a solution of 2',2'-difluorodeoxyribofuranosylcytosine (Gemcitabine) (0.42g, 1.6 mmol) in 30 ml DMF was added 0.81 ml DMF containing 1.6 mmol HCl(g) followed by a solution of elaidic acid chloride (0.51 g, 1.7 mmol) in 3 ml DMF and the reaction mixture was stirred at ambient temperature for 12 hours. The solvent was evaporated at high vacuum and the crude product was purified on a column of silica gel with 15% methanol in chloroform as the eluent system. The impure fractions were repurified to give a total of 0.25 g (30%) of the title compound.

$^1$H NMR (DMSO-$d_6$ 300 MHz) δ: 7.5(1H, d, ArH), 7.45 (2H, br. s, $NH_2$), 6.45(1H, d, —OH), 6.17(1H, t, CH-1'), 5.8(1H, d, ArH), 5.35(2H, m, CH=CH), 4.4–4.05(3H, m, $CH_2$-5' and CH-4'), 3.95(1H, m, CH-3'), 2.35(2H, t, $CH_2$—COO), 1.95(4H, m, $CH_2$—CH=), 1.55(2H, m, $CH_2$—C—COO), 1.25(20H, m, $CH_2$), 0.85(3H, t, $CH_3$). $^{13}$C NMR (DMSO-$d_6$, 75 MHz) δ: 172.67(COO), 165.63(C-4) 154.51 (C-2), 141.12(C-6), 130.08 and 130.03(C-9"/C-10"), 126.09, 122.67 and 119.24(t, C-2'), 94.86(C-5), 83.90(C-1'), 77.36(C-4'), 70.41, 70.11 and 69.80(t, C-3'), 62.53(C-5'), 33.24, 31.95, 31.29, 29.00, 28.94, 28.84, 28.72, 28.50, 28.43, 28.33, 24.34, 22.11 ($CH_2$), 13.94($CH_3$).

In addition, a small amount (0.05 g) of the Elaidic acid (3')-Gemcitabine ester was isolated from impure fractions.

$^1$H NMR (DMSO-$d_6$, 300 MHz) δ: 7.65(1H, d, ArH), 7.40(2H, d, $NH_2$), 6.25(1H, t, CH-1'), 5.82(1H, d, ArH), 5.4–5.2(4H, m, OH-5', CH=CH and CH-3'), 4.15(1H, m, CH-4'), 3.85–3.55(2H, m, $CH_2$-5'), 2.45(2H, t, $CH_2$—COO), 1.95(2H, m, $CH_2$—C=), 1.55(2H, m, $CH_2$—C—COO), 1.25(20H, m, $CH_2$), 0.85(3H, t, $CH_3$).

$^{13}$C NMR (DMSO-$d_6$, 75 MHz) δ: 171.70(COO), 165.69 (C-4), 154.46(C-2), 141.30(C-6), 130.10 and 130.03(C-9"/C-10"), 125.17, 121.72 and 118.27(t, C-2'), 94.78(C-5), 83.78(C-1'), 78.41(C-4'), 69.93, 69.60 and 69.30(t, C-3'), 59.15(C-5'), 32.95, 31.93, 31.26, 28.98, 28.90, 28.81, 28.69, 28.46, 28.28, 28.23, 24.26, 22.09($CH_2$), 13.95($CH_3$).

EXAMPLE 2

Elaidic Acid ($N^4$)-Gemcitabine Amide

To a solution of 2',2'-difluorodeoxyribofuranosylcytosine (Gemcitabine) (0.38 g, 1.3 mmol) in 5 ml pyridine was added elaidic acid chloride (0.57 g, 1.9 mmol) and the reaction mixture was stirred at ambient temperature for 2.5 hours.

The solvent was evaporated at high vacuum and the crude product was purified on a column of silica gel with 15% methanol in chloroform as the eluent system. Product containing fractions were evaporated, and the residue was treated with ether/hexan in an ultra-sound bath. The crystalline material was dried to give 0.1 g (15%) of the title compound.

$^1$H NMR (DMSO-$d_6$ 300 MHz) δ: 10.95(1H, s, NHCO), 8.25(1H, d, ArH), 7.25(1H, d, ArH), 6.30(1H, d, —OH), 6.15(1H, t, CH-1'), 5.35(2H, m, CH=CH), 5.30(1H, t, —OH), 4.2(1H, m, CH-4'), 3.9–3.6(3H, m, CH-3' and $CH_2$-5'), 2.35(2H, t, $CH_2$-CON), 1.95(2H, m, $CH_2$—C=), 1.55 (2H, m, $CH_2$—C—COO), 1.25(20H, m, $CH_2$), 0.85(3H, t, $CH_3$).

$^{13}$C NMR (DMSO-$d_6$, 75 MHz) δ: 174.06(CONH) 162.89 (C-4), 154.22(C-2), 144.69(C-6), 130.04(C-9"/C-10"), 122.94($J_{CF}$=259Hz, C-2'), 95.91(C-5), 84.11($J_{CF}$=31Hz,

C-1'), 81.02(C-4'), 68.35($J_{CF}$=22Hz, C-3'), 58.76(C-5'), 36.38, 31.94, 31.28, 28.99, 28.83, 28.71, 28.56, 28.48, 28.30, 24.34, 22.10($CH_2$), 13.94 ($CH_3$).

Preferred Gemcitabine derivatives of this invention have a higher therapeutic value for treating malignant diseases than Gemcitabine itself. This has been shown in two different in-vivo models with both single and repeated dosing. For single dose treatment, the effect of the derivatives are better or comparable to Gemcitabine. This is especially pronounced for the amide derivative where superior effect is obtained with just 25% of the Gemcitabine dose.

At repeated dosing, the difference between the derivatives and Gemcitabine is even more striking. This is reflected both in increased survival time and in long term survivors. Another striking feature is the toxicity observed with Gemcitabine itself at both top and mid range repeated dosing. Although the effect obtained with the no-tox-low-range dose (1 mg/kg) is good, it is exceeded by both the $N^4$-amide and the 5'-ester derivatives. Gemcitabine has an optimal effect at a plasma concentration of about 20 $\mu$M but higher concentrations, above 35 $\mu$M, inhibit the anti-cancer effect due to saturation of the phosphorylation mechanism. (Gandhi, Cellular Pharmacology of Gemcitabine in Gemcitabine: Rationales for Clinical Trial Design and Evaluation, Mini Symposium, 12.3.96, Vrije Universiteit Amsterdam). In contrast, preferred Gemcitabine derivatives of the invention yield an optimal plasma level of Gemcitabine for a prolonged time without reaching inhibitory concentrations (>35 $\mu$M). This may be because the derivatives are not subject to phosphorylation and probably not an inhibitor of the mechanism either.

A main problem in cancer treatment is development of resistance to therapy. Multi drug resistance (MDR) is one of the principal reasons for failure of otherwise effective drugs. We have found that the preferred derivatives of this invention somehow block the MDR-pump, and hence circumvent this problem.

The cellular uptake of nucleosides and nucleoside analogues such as gemcitabine is mainly via the selective Nucleoside Transport (NT) receptor.

Modulation/inhibition of this receptor may be seen as resistance to the drug in a clinical situation. This phenomenon can be observed in-vitro through addition of NT inhibitors. We have surprisingly seen that our derivatives are not influenced by the presence of NT inhibitors, since the cytostatic activity of the preferred derivatives is conserved in the presence of such inhibitors.

The half-life of Gemcitabine in plasma is approximately 10 minutes, due to rapid deamination by the endogenous enzyme deoxycytidine deaminase to the corresponding uracil derivative (P. G. Johnston et al, Cancer Chromatography and Biological Response Modifiers, Annual 16, 1996, Chap. 1, ed. Pinedo H. M. et al.).

In contrast, the derivatives of this invention are poor substrates for the deactivating enzyme, and therefore their half-life is increased. Consequently, the derivatives of this invention are more suited than Gemcitabine itself for systemic or local treatment of malignant tumours.

The new compounds of this invention are not only potentially useful in the treatment of cancer, but also have activity as anti-viral agents.

BIOLOGY

Experimental

The cytoxicity activity of Gemcitabine-$N^4$-elaidic amide and Gemcitabine-5'-elaidic ester were investigated in 2 pairs of rodent and human tumour cell lines, each consisting of a parent line and a subline either resistant or cross-resistant to Gemcitabine.

The cell lines were the human ovarian tumour line A2780 and subline AG6000 which is resistant to Gemcitabine and has a deficiency of deoxycytidine kinase, and the murine colon tumour line C26A and the subline C26G with no altered deoxycytidine kinase but a 10-fold decrease in thymidine kinase I. The cytotoxicity of each compound was evaluated following continuous drug exposure for 72 hours. The cell numbers were determined by SRB assay, and percentage growth inhibition was calculated for each tumour line as IC50 value, given in $\mu$M, that is the concentration of the compound giving rise to a 50% growth inhibition compared to control.

Results

The IC50 value in $\mu$M of cytotoxicity activity of Gemcitabine itself in comparison to cytoxicity activity of Gemcitabine-$N^4$-elaidic amide and Gemcitabine-5'-elaidic ester are shown in the table below. The acitivity of the derivatives of the Gemcitabine is much greater than the cytotoxic activity of Gemcitabine in the cell lines tested.

TABLE

The cytotoxicity of Gemcitabine, Gemcitabine-$N^4$-elaidic amide and Gemcitabine-5'-elaidic ester in IC50 ($\mu$M) values in the cell lines C26-A, C26-G, A2780 and AG6000

|  | C26-A | C2G-G | A2780 | AG6000 |
|---|---|---|---|---|
| Gemcitabine | 0.0055 | 0.0075 | 0.0005 | 100 |
| Gemcitabine-$N^4$-elaidic amide | <0.0001 | <0.0001 | <0.0001 | 35 |
| Gemcitabine-5'-elaidic ester | 0.0003 | 0.0005 | <0.0001 | 100 |

The cytostatic activity of gemcitabine and gemcitabine-5'-elaidic acid ester in CEM cells was determined with and without the nucleoside transport modifiers Nitrobenzylthioinosine (NBMPR) or Persantine (Pyridamole). As can be seen from the table below, the $IC_{50}$ gemcitabine is > two-fold higher than the $IC_{50}$ gemcitabine-5'-elaidic acid ester. With the addition of NT inhibitors, there is a ten-fold rise in the $IC_{50}$ gemcitabine values, while the $IC_{50}$ gemcitabine-5'-elaidic acid ester is little affected (1.3–1.5 increase). In the "resistant" situation, the preferred derivative is 15–20 fold more potent then the mother drug.

| Compound | $IC_{50}$ $\mu$M<br>No inhibitor | $IC_{50}$ $\mu$M<br>NBMPR<br>100 $\mu$M | $IC_{50}$ $\mu$M<br>Persantine<br>4 $\mu$g/ml |
|---|---|---|---|
| Gemcitabine | 0.11 ± 0.01 | 1.11 ± 0.08 | 1.26 ± 0.04 |
| Gemcitabine-5'-elaidic acid ester | 0.047 ± 0.006 | 0.072 ± 0.034 | 0.065 ± 0.023 |

The anti tumour effect of Gemcitabine-$N^4$-elaidic amide or Gemcitabine-5'-elaidic ester were investigated in-vivo in mice in two different tumour types, both with single and repeated dosing Effect of Gemcitabine-$N^4$-elaidic Amide or Gemcitabine-5'-elaidic Ester on Co-26 Inoculated Intrasplenic to Mice Balb/c female mice were inoculated with the murine colon cancer Co-26 in the spleen on day 0. In this model, tumours develop mainly in the liver. Intraperitoneal treatment was started on day 1. Single doses of the compounds were tested in comparison with Gemcitabine at single dose. Saline was used as control.

| No. Mice | Substance | Dose mg/kg | Mean survival time T/C [%] | Long term survivors (>35 d) | Toxic deaths |
|---|---|---|---|---|---|
| 10 | Saline | | | | |
| 8 | Gemcitabine-$N^4$-elaidic amide | 25 | 103.7 | 5/8 | 1/8 |
| 7 | Gemcitabine-5'-elaidic ester | 75 | 128.6 | 1/7 | 0/7 |
| 7 | Gemcitabine-5'-elaidic ester | 100 | 100.1 | 4/7 | 0/7 |
| 7 | Gemcitabine | 75 | 132.8 | 2/7 | 0/7 |
| 7 | Gemcitabine | 100 | 116.2 | 4/7 | 0/7 |

Mean survival time for the animals that died were in the same range for the compounds tested. Gemcitabine-$N^4$-elaidic amide was superior to Gemcitabine-5'-elaidic ester and Gemcitabine with 5/8 survivors at a dose of only 25 mg/kg compared to Gemcitabine at 100 mg/kg.

In parallel experiment, dosing was repeated on days 1–11

| No. Mice | Substance | Dose mg/kg | Mean survival time T/C [%] | Long term survivors (>46 d) | Toxic deaths |
|---|---|---|---|---|---|
| 10 | Saline | | | | |
| 8 | Gemcitabine-$N^4$-elaidic amide | 1 | 155 | 2/8 | 0/8 |
| 8 | Gemcitabine-$N^4$-elaidic amide | 4 | 185.6 | 1/8 | 0/8 |
| 8 | Gemcitabine-5'-elaidic ester | 1 | 150.6 | 1/8 | 0/8 |
| 8 | Gemcitabine-5'-elaidic ester | 4 | 166.9 | 3/8 | 2/8 |
| 8 | Gemcitabine | 1 | 170.6 | 2/8 | 1/8 |
| 8 | Gemcitabine | 4 | toxic | 0/8 | 8/8 |

In this experiment the results obtained with Gemcitabine-$N^4$-elaidic amide and low dose Gemcitabine-5'-elaidic ester were better or equal to results obtained with the low dose of Gemcitabine. Although the high dose of Gemcitabine-5'-elaidic ester is slightly toxic, it is less so than the dose of Gemcitabine itself.

Effect of Gemcitabine-N4-elaidic Amide or Gemcitabine 5'-elaidic Ester on P-388 ip in Mice, Single Doses or Repeated Doses B6D2F1 female mice were implanted with the murine lymphatic leukaemia P 388 cells intraperitoneally. Treatments were initiated on day 1 post implantation of cells intraperitoneally. Mean survival time, long term survivors and toxic deaths were recorded following single dose treatment, repeated dose treatment for 5 days and repeated dose treatment for 10 days. The results are presented in the tables below. Single dose treatment with Gemcitabine-5'-elaidic ester was effective with prolonged survival time and long term survivor observed compared to the same dose of Gemcitabine.

Single Dose Treatment

| No. Mice | Substance | Dose mg/kg | Mean survival time T/C [%] | Long term survivors (>35 d) | Toxic deaths |
|---|---|---|---|---|---|
| 9 | Saline | | | | |
| 6 | Gemcitabine-5'-elaidic ester | 75 | 186.3 | 1/6 | 0/6 |
| 6 | Gemcitabine-5'-elaidic ester | 100 | 138.9 | 0/6 | 0/6 |
| 6 | Gemcitabine | 75 | 138.9 | 0/6 | 0/7 |

Repeated dose treatment, days 1–4

| No. Mice | Substance | Dose Mg/kg | Mean survival time T/C (%) | Long term survivors (>35 d) | Toxic deaths |
|---|---|---|---|---|---|
| 8 | Saline | | | | |
| 6 | Gemcitabine-$N^4$-elaidic amide | 1 | 178 | 2/6 | 0/6 |
| 6 | Gemcitabine-$N^4$-elaidic amide | 4 | 183 | 1/6 | 0/6 |
| 6 | Gemcitabine | 15 | 58.0 | 0/6 | 6/6 |

Activity of Gemcitabine-$N^4$-elaidic amide was clear-cut at repeated doses days 1–4 with long term survivors observed and prolonged mean survival time both at 1 and 4 mg/kg. In the control group treated with Gemcitabine at 15 mg/kg all animals died of toxicity.

Repeated dose treatment, treatment days 1–11

| No. Mice | Substance | Dose mg/kg | Mean survival time T/C [%] | Long term survivors (>45 d) | Toxic deaths |
|---|---|---|---|---|---|
| 9 | Saline | | | | |
| 6 | Gemcitabine-$N^4$-elaidic amide | 1 | 172.5 | 1/6 | 0/6 |
| 6 | Gemcitabine-$N^4$-elaidic amide | 4 | 215.7 | 0/6 | 0/6 |
| 6 | Gemcitabine-5'-elaidic ester | 1 | 317.0 | 0/6 | 0/6 |
| 6 | Gemcitabine-5'-elaidic ester | 4 | 220.6 | 2/6 | 0/6 |
| 6 | Gemcitabine | 1 | 178.8 | 0/6 | 0/6 |
| 6 | Gemcitabine | 4 | 71.9 | 0/6 | 0/6 |

Treatment for 10 days increased the anti tumour activity compared to shorter treatment. Toxicity of Gemcitabine was larger on a mg/kg basis, with 6/6 toxic deaths at 4 mg/kg. Long term survivors were observed post repeated treatment with both Gemcitabine-$N^4$-elaidic amide and Gemcitabine-5'-elaidic ester, and substantially increased mean survival times were observed for both Gemcitabine-$N^4$-elaidic amide and Gemcitabine-5'-elaidic ester.

The Gemcitabine esters or amides of the present invention may be administered systemically, either enterally or parenterally.

For enteral administration, the active compounds of the present invention may be presented as, e.g. soft or hard gelatine capsules, tablets, granules, grains or powders, drags, syrups, suspensions or solutions.

When administered parenterally, preparations of the Gemcitabine esters or amides as injection or infusion solutions, suspensions or emulsions are suitable.

The preparation can contain inert or pharmacodynamically active additives, as well known to those skilled in the formulation arts. For instance, tablets or granulates can contain a series of binding agents, filler materials, emulsifying agents, carrier substances or dilutes. Liquid preparations may be present, for example in the form of a sterile solution.

Capsules can contain a filler material or thickening agent in addition to the active ingredient. Furthermore, flavour-improving additives as well as the substances usually used as preserving, stabilising, moisture-retaining and emulsifying agents, salts for varying the osmotic pressure, buffers and other additives may also be present.

The dosage in which the preparations according to this invention are administered will vary according to the mode of use and route of use, as well as to the requirements of the patient. In general a daily dosage for a systemic therapy for an adult average patient will be about 0.1–150 mg/kg body weight/day, preferably 1–40 mg/kg/day. For topical administration, an ointment, for instance, can contain from 0.1–10% by weight of the pharmaceutical formulation, especially 0.5–5% by weight.

If desired, the pharmaceutical preparation containing the Gemcitabine esters or amides can contain an antioxidant, e.g. tocopherol, N-methyl-tocophermine, butylated hydrocyanisole, ascorbic acid or butylated hydroxytoluene.

Combination therapies, i.e. in which the administration of a Gemcitabine ester or amide of this invention is carried out in conjunction with other therapies, e.g. surgery, radiation treatment and chemotherapy, are also contemplated. For example, the preferred treatment of brain tumours seems likely to be a combination of surgery and treatment with a Gemcitabine ester or amide of this invention by systemic or local administration.

What is claimed is:

1. A Gemcitabine derivative having the formula (I):

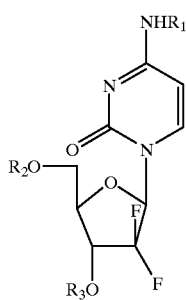

(I)

wherein $R_1$, $R_2$ and $R_3$ are independently selected from hydrogen and $C_{18}$- and $C_{20}$-saturated and monounsaturated acyl groups, with the proviso that $R_1$, $R_2$ and $R_3$ cannot all be hydrogen.

2. A compound according to claim 1, wherein only one of $R_1$, $R_2$ and $R_3$ is a said acyl group.

3. A compound according to claim 2, wherein said mono-acyl substitution is at the 3'-O or 5'-O position of the sugar moiety.

4. A compound according to claim 3, wherein said mono-acyl substitution is at the 5'-O position of the sugar moiety.

5. A compound according to claim 1, 2, 3, or 4, wherein $R_1$, $R_2$ and $R_3$ are selected from the group consisting of oleoyl, elaidoyl, cis-eicosenoyl and trans-eiconsenoyl.

6. Elaidic acid (5')-Gemcitabine ester.

7. Elaidic acid ($N^4$)-Gemcitabine amide.

8. A pharmaceutical composition, comprising a Gemcitabine ester or amide according to claim 1, 2, 3, 4, 6, or 7, and a pharmaceutically acceptable carrier or excipient.

9. A process for preparing a Gemcitabine derivative as defined in claim 1, characterized by reacting Gemcitabine with a compound of the formula:

FaX wherein Fa is an acyl group of a monounsaturated $C_{18}$ or $C_{20}$ fatty acid, and X is a leaving group.

10. A pharmaceutical composition comprising (a) a Gemcitabine derivative according to claim 1, 2, 3, or 4, wherein $R_1$, $R_2$ and $R_3$ are selected from the group consisting of oleoyl, elaidoyl, cis-eicosenoyl and trans-eiconsenoyl and (b) a pharmaceutically acceptable carrier or excipient for said derivative.

11. In a method of treating a patient for cancer that includes administering Gemcitabine to the patient, the improvement wherein the Gemcitabine is in a derivatized form corresponding to the formula (I)

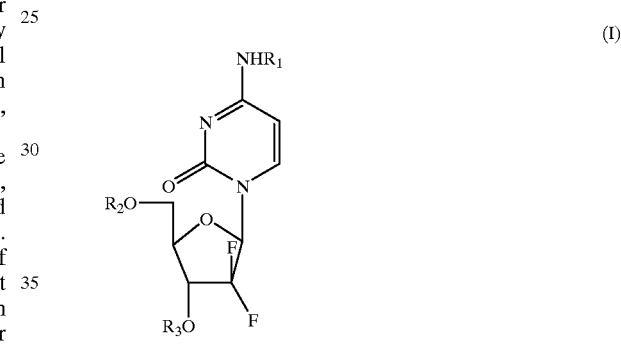

(I)

wherein $R_1$, $R_2$, and $R_3$ are independently selected from the group consisting of hydrogen and $C_{18}$ and $C_{20}$ saturated and monounsaturated acyl groups, with the proviso that $R_1$, $R_2$, and $R_3$ cannot all be hydrogen.

12. The method of claim 11, wherein only one of $R_1$, $R_2$, and $R_3$ is a said acyl group.

13. The method of claim 12, wherein the Gemcitabine is administered at a dosage level of about 0.1–150 mg per kg of body weight per day.

14. The method of claim 12, wherein the cancer is a melanoma or is in at least one of the RES, lungs, pancreas, intestines, esophagus, uterus, ovaries, and mammae.

15. The method of claim 12, wherein said mono-acyl substitution is at the 3'-O or 5'-O position of the sugar moiety.

16. The method of claimed 15, wherein said mono-acyl substitution is at the 5'-O position of the sugar moiety.

17. A method according to claim 11, 12, 15, or 16, wherein $R_1$, $R_2$ and $R_3$ are selected from the group consisting of oleoyl, elaidoyl, cis-eicosenoyl and trans-eiconsenoyl.

18. In a method of treating a patient for cancer that includes administering Gemcitabine to the patient, the improvement wherein the Gemcitabine is in the form of Elaidic acid (5')-Gemcitabine ester.

19. The method of claim 18, wherein the Gemcitabine is administered at a dosage level of about 1–40 mg per kg of body weight per day.

20. The method of claim 18, wherein the cancer is ovarian cancer.

21. The method of claim 18, wherein the cancer is colon cancer.

22. In a method of treating a patient for cancer that includes administering Gemcitabine to the patient, the improvement wherein the Gemcitabine is in the form of Elaidic acid ($N^4$)-Gemcitabine amide.

23. The method of claim 22, wherein the Gemcitabine, is administered at a dosage level of about 1–40 mg per kg of body weight per day.

24. The method of claim 22 wherein the cancer is ovarian cancer.

25. The method of claim 22, wherein the cancer is colon cancer.

26. In a method of treating a patient for a viral infection that includes administering Gemcitabine to the patient, the improvement wherein the Gemcitabine is in a derivatized form corresponding to the formula (I):

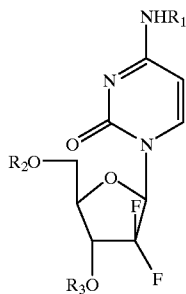

(I)

wherein $R_1$, $R_2$, and $R_3$ are independently selected from the group consisting of hydrogen and $C_{18}$ and $C_{20}$ saturated and monounsaturated acyl groups, with the proviso that $R_1$, $R_2$, and $R_3$ cannot all be hydrogen.

27. The method of claim 26, wherein only one of $R_1$, $R_2$, and $R_3$ is a said acyl group.

28. The method of claim 27, wherein said mono-acyl substitution is at the 3'-O or 5'-O position of the sugar moiety.

29. The method of claim 28, wherein said mono-acyl substitution is at the 5'-O position of the sugar moiety.

30. A method according to claim 26, 27, 28, or 29, wherein $R_1$, $R_2$ and $R_3$ are selected from the group consisting of oleoyl, elaidoyl, cis-eicosenoyl and trans-eiconsenoyl.

31. In a method of treating a patient for a viral infection that includes administering Gemcitabine to the patient, the improvement wherein the Gemcitabine is in the form of: Elaidic acid (5')-Gemcitabine ester.

32. In a method of treating a patient for a viral infection that includes administering Gemcitabine to the patient, the improvement wherein the Gemcitabine is in the form of Elaidic acid ($N^4$)-Gemcitabine amide.

* * * * *

UNITED STATES PATENT AND TRADEMARK OFFICE
CERTIFICATE OF CORRECTION

PATENT NO. : 6,384,019 B1
DATED : May 7, 2002
INVENTOR(S) : Myhren et al.

It is certified that error appears in the above-identified patent and that said Letters Patent is hereby corrected as shown below:

Column 1,
Line 5, "5" should be deleted.

Column 2,
Line 35, "$\underset{-\text{HX}}{\xrightarrow{Base}}$" should read -- $\underset{-\text{HX}}{\xrightarrow{Base}}$ --.

Column 4,
Line 19, "$^{13}$C NMR" should begin a new paragraph; and
Line 54, "ether/hexan" should read -- ether/hexane --.

Column 9,
Line 6, "drags," should read -- dragées --; and
Line 14, "dilutes." should read -- diluents. --.

Signed and Sealed this

Twenty-second Day of October, 2002

*Attest:*

JAMES E. ROGAN
*Attesting Officer*     *Director of the United States Patent and Trademark Office*